United States Patent
Atluri

(10) Patent No.: US 11,327,037 B2
(45) Date of Patent: May 10, 2022

(54) SENSING MATERIALS, METHOD FOR MAKING FUNCTIONAL DEVICES AND APPLICATIONS THEREOF

(71) Applicant: Innoscentia AB, Malmö (SE)

(72) Inventor: Rambabu Atluri, Malmö (SE)

(73) Assignee: Innoscentia AB, Malmö (SE)

( * ) Notice: Subject to any disclaimer, the term of this patent is extended or adjusted under 35 U.S.C. 154(b) by 0 days.

(21) Appl. No.: 16/498,756

(22) PCT Filed: Mar. 12, 2018

(86) PCT No.: PCT/SE2018/050236
§ 371 (c)(1),
(2) Date: Sep. 27, 2019

(87) PCT Pub. No.: WO2018/182481
PCT Pub. Date: Oct. 4, 2018

(65) Prior Publication Data
US 2020/0041434 A1 Feb. 6, 2020

(30) Foreign Application Priority Data
Mar. 31, 2017 (SE) .................................. 1750391-3

(51) Int. Cl.
*G01N 27/12* (2006.01)
*G01N 33/00* (2006.01)

(52) U.S. Cl.
CPC ....... *G01N 27/125* (2013.01); *G01N 33/0047* (2013.01)

(58) Field of Classification Search
CPC .. G01N 27/12; G01N 27/125; G01N 33/0027; G01N 33/0047
See application file for complete search history.

(56) References Cited

U.S. PATENT DOCUMENTS

| 4,067,695 A * | 1/1978 | Miyaguchi ............. G01N 27/12 338/34 |
| 4,249,156 A * | 2/1981 | Micheli ................... C04B 35/46 338/34 |
| 8,880,448 B2 | 11/2014 | Haddad et al. |
| 2003/0129085 A1 * | 7/2003 | Suslick .................. G01N 31/22 422/400 |
| 2003/0175411 A1 * | 9/2003 | Kodas .................. H01G 4/1227 427/58 |

(Continued)

FOREIGN PATENT DOCUMENTS

| CA | 2 742 967 | 5/2010 |
| CN | 105980849 | 9/2016 |

(Continued)

OTHER PUBLICATIONS

International Search Report dated Apr. 27, 2018 in PCT/SE2018/050236.

(Continued)

*Primary Examiner* — Benjamin R Schmitt
(74) *Attorney, Agent, or Firm* — Grüneberg and Myers PLLC

(57) ABSTRACT

A functional device has a functional sensor, which includes a sensor part and interdigitated electrode arrays. The sensor part includes a sensing material, and the interdigitated electrode arrays are printed electrodes.

12 Claims, 3 Drawing Sheets

(56) References Cited

U.S. PATENT DOCUMENTS

Figure 1A:
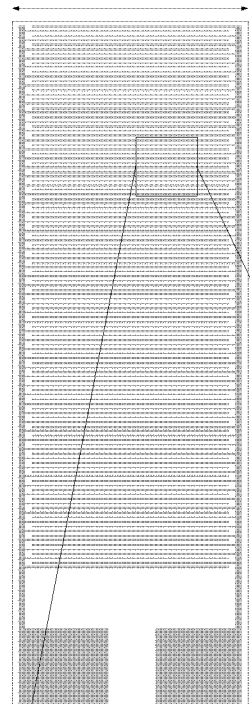

| | | | |
|---|---|---|---|
| 2003/0180446 A1* | 9/2003 | Totokawa | G01N 27/12 427/58 |
| 2005/0036020 A1* | 2/2005 | Li | C09D 11/52 347/100 |
| 2006/0014005 A1* | 1/2006 | Basco | C09D 11/30 428/209 |
| 2006/0191319 A1 | 8/2006 | Kurup | |
| 2007/0028667 A1* | 2/2007 | Kim | G01N 33/0031 73/23.34 |
| 2008/0143351 A1* | 6/2008 | Lee | G01N 27/07 324/698 |
| 2011/0045601 A1* | 2/2011 | Gryska | G01N 27/221 436/149 |
| 2011/0291806 A1 | 12/2011 | Hoofman et al. | |
| 2012/0049864 A1* | 3/2012 | Han | G01N 27/127 324/649 |
| 2012/0242355 A1* | 9/2012 | Kato | G01N 27/125 324/700 |
| 2016/0195488 A1* | 7/2016 | Ensor | G01N 27/227 422/69 |
| 2017/0052160 A1 | 2/2017 | Olsson | |

FOREIGN PATENT DOCUMENTS

| | | |
|---|---|---|
| JP | H8-15195 | 1/1996 |
| JP | 2000-28562 | 1/2000 |
| WO | 01/13087 | 2/2001 |
| WO | 03/044521 | 5/2003 |
| WO | 2014/143291 | 9/2014 |
| WO | 2015035243 | 3/2015 |
| WO | 2015/142289 | 9/2015 |
| WO | 2015/150880 | 10/2015 |

OTHER PUBLICATIONS

Written Opinion dated Apr. 27, 2018 in PCT/SE2018/050236.

Nguyen et al., "*Toward hydrogen detection at room temperature with printed ZnO nanoceramics films activated with halogen lighting*", Applied Surface Science 357 (2015) 14-21 doi 10.1016/j.apsusc.2015.08.137 0169-4332.

Sahu et al., "*Development of nanocrystalline ZnO-SnO$_2$ composite based platform for gas sensing applications*", 2016 IEEE Uttar Pradesh Section International Conference on Electrical, Computer and Electronics Engineering (UPCON), Indian Institute of Technology (Banaras Hindu University), Varanasi, India, Dec. 9-11, 2016, p. 142-145.

Kaya, et al., "*Effect of pyrene substitution on the formation and sensor properties of phthalocyanine-single walled carbon nanotube hybrids* ", Sensors and Actuators: B 199, 2014, pp. 277-283.

Liu, et al., *"Design of Single Chip Integration of MWNTs/SiO$_2$ Humidity Sensor and its Interface ASIC "*, International Conference on Optoelectronics and Microelectronics (ICOM), Aug. 23-25, 2012, pp. 470-473.

Mun, et al., "*Cellulose-Titanium dioxide-multiwalled carbon nanotube hybrid nanocomposite and its ammonia gas sensing properties at room temperature*", Snesors and Actuators: B 171-172, 2012, pp. 1186-1191.

Paolesse, et al., "*Porphyrinoids for Chemical Sensor Applications* ", Chemical Reviews 117, 2017, pp. 2517-2583.

Ueda, et al., "Preparation of single-walled carbon annotube/ TiO$_2$hybrid atmospheric gas sensor operated at ambient temperature", Diamon & Related Materials 18, 2009, pp. 493-496.

Chinese Office Action dated Oct. 26, 2021 in Chinese Application No. 201880019038.X, with partial English translation, 14 pages.

\* cited by examiner

SENSING MATERIALS, METHOD FOR MAKING FUNCTIONAL DEVICES AND APPLICATIONS THEREOF

This application is a National Stage entry under § 371 of International Application No. PCT/SE2018/050236, filed on Mar. 12, 2018, and which claims the benefit of Swedish Application No. 1750391-3, filed on Mar. 31, 2017.

FIELD OF THE INVENTION

The present disclosure generally relates to sensor materials and a process for making functional devices thereof. More particularly the invention generally relates to sensing materials with gas sensing functions, materials with optimal conductivity and printability, processes of manufacturing said materials, processes of applying such materials for making functional devices, processes for integrating of said devices with existing electronic components and products, and other embodiments thereof.

TECHNICAL BACKGROUND

Functional devices capable of odor detection, chemical detection, and gas detection have emerged as a powerful tool for the detection of chemically diverse analytes. The devices consist of a sensing part and an electronic component. The sensing part can be an array of several different sensing elements or a single device or a combination of both. Traditionally the functional devices are referred as an electronic nose or e-sensing devices. In a broader sense, the functional device is referred to gas sensors that measure the ambient gas atmosphere based on the general principle that changes in the gaseous atmosphere alter the sensor properties in a characteristic way.

The devices with gas sensing function are not new, and they have been in use since the 1980s. However, the practical use of the sensor, in particular, food waste is still under extensive evaluation. There are no quantitative means to determine if packaged food is spoiled in the food chain. This is because, difficulties in robustness, selectivity, and reproducibility of the sensors are still challenging. Also, sensor cost on food industry is always market driven and have been the issue of such sensors to enter food and consumer products. More importantly, consumers are demanding more simple way of communicating information of spoilage such as digital rather than analog display.

The following known means of addressing the issues and state of the art following the invention. The document WO2015150880 discloses an electronic nose for the determination of the meat freshness. The purpose of the invention is achieved by using a gas sensor system, a processor, a wireless Bluetooth module and smart device with the video output device for processing the signals and presenting the measurement results. The document disclose that the device is a portable electronic nose, which analyses volatile compounds and gasses in the meat headspace; however, the device cannot be placed on each packaged food. Also, a distance from the sensors to the surface of the meat is less than 10 mm, which opens concerns over food regulation and may limit the application of the sensor on food packages.

Food package with integrated RFID-tag and a sensor is disclosed in US20110291806; wherein the invention relates to a container configured for containing a substance and comprising electronic circuitry for sensing a physical property of the substance and providing a wireless signal indicative of the physical property sensed. The container comprises a battery for powering the electronic circuitry, implying an expensive solution for food packaging industry.

The document WO2015142289 discloses a sensor comprising a semi-permeable film layer, said semi-permeable film layer comprising at least one integrally formed well having at least one sensing element disposed of therein.

An encased polymer nanofiber-based electronic nose is disclosed in WO2014143291. The system includes the chemical sensor, an impedance measuring device coupled to the electrodes and configured to determine an electrical impedance of the plurality of fibers, and an analyzer configured to identify the chemical species based on a change in the electrical impedance. However, the chemical species are identified based on computer analyzer and may not be compatible with packaged food. Also, the fibers used were nano-fibers and swell during the exposure to chemical species and demands high headspace to the chemical environment.

In yet another document, U.S. Pat. No. 8,880,448, a method of predicting odor pleasantness with an electronic nose is disclosed.

The document US20060191319 discloses a probe such as a penetrometer to detect the presence of chemicals in the subsurface or underground locations. However, the application of the sensing probe used to identify or characterize foods having a particular olfactory pattern such as coffee.

The document WO2003044521 relates to a remotely readable sensor for indication of usability condition of perishable products such as foodstuffs and medical drugs. The functional material disclosed is only oxygen or sulfur indicator but in general other compounds such as amines, ketones, alcohols etc generated in the atmosphere of the foodstuff package and this part is not readable by the functional material.

The document CA2742967 relates to a temperature sensor unit comprises a solid wax and gas-filled polymeric particles. The wax is a food-grade wax such as cheese wax, and the polymer particles are preferably air-filled polystyrene microcapsules of mean particle diameter 50-500 μm. The invention has particular utility in refrigeration and freezer systems for foodstuffs and the like. However, the sensor may not provide spoilage level of the food and relies mostly on the surrounding temperatures.

In yet another document WO2001013087, a sensor capable of detecting the analyte wherein the presence of the analyte is indicative of the disease is disclosed. The sensor includes a first material having a positive temperature coefficient of resistance and a second non-conductive or insulating material compositionally different than the first material that shows an increased sensitivity detection limit for polar and non-polar analytes.

Although the preceding systems have some usefulness, there remains a need in the art for a low cost, broadly responsive analyte detection sensor and printability of the sensing materials. The present invention aims to solve and address many of the issues above. Accordingly, there is a need for a robust sensor device which accurately, simply and rapidly detects a range of analytes and more importantly, presents printability and processability of the sensor material to make a functional device remains.

SUMMARY OF THE INVENTION

The present invention relate to a functional device having a functional sensor comprising of a sensor part and interdigitated electrode arrays, wherein the sensor part comprises a sensing material and, the interdigitated electrode arrays are printed electrodes.

In one embodiment the sensing material is a composite comprising two or more materials wherein one of the materials is optionally an additive, and the other material/materials is/are selected from the group consisting of non-conducting material, semi-conducting material, and conducting material.

In one embodiment the non-conducting material is a synthetic amorphous silica, preferably selected from the group consisting of fumed silica, precipitated porous silica, precipitated non-porous silica and silica aerogel, wherein the non-conducting material is also synthetic titanium dioxide, preferably selected from the group consisting of precipitated porous titanium dioxide, and precipitated non-porous titanium dioxide.

In one embodiment the conducting material selected from the group consisting of carbon and carbon based materials, preferably where in the carbon and carbon based materials are selected from the group consisting of carbon dots, carbon nanoparticles, carbon sheets, carbon nanotubes, and graphenes.

In one embodiment the semi-conducting material is a metalloporphyrin dye; preferably the metalloporphyrin dye comprise at least one metal ion selected from the group consisting of $Sc^{3+}$, $Zr^{4+}$, $Lu^{3+}$, $Cr^{3+}$, $Mn^{3+}$, $Fe^{3+}$, $Co^{3+}$, $Mo^{5+}$, $Ru^{2+}$, and $Mg^{2+}$; and preferably the metalloporphyrin dye comprise alkyl or aryl groups with R a minimum of 4.

In one embodiment the semi-conducting material is a composite of silica, or silicon, and carbon; wherein the molar ratios of composite between Si to C varies between 0.01 to 1, preferably between 0.2 to 0.6.

In one embodiment said additive is a binder; preferably one selected from the group consisting of nitrocellulose, polyurethane resins, polyvinylbutyral, PVC-copolymers, ketonic resins, fumaric & maleic resins, polyamides, ethylcellulose, and acrylic resins.

In one embodiment the printed electrodes are arranged at a distance, wherein the distance may vary between 100 nm to 1000 µm, preferably between 100 nm to 500 µm; preferably between 5 µm to 200 µm; preferably the printed electrodes may be screen printed or lithographic printed or ink jet printed electrodes.

In one embodiment the functional device may be integrated with electronic components, preferably wherein the electronic components are passive, active or battery-assisted passive tags, preferably wherein the said components frequency range between 9 KHz to 3000 GHz, preferably between 13.56 MHz to 960 MHz.

In one embodiment the functional device may be integrated with electronic components, preferably a circuit, where in the circuit comprises of two or more transistors.

Another aspect of the present invention relates to a method of making a functional device according to further embodiments, wherein the method comprises:

a) adding a sensing material to a solvent capable of forming a slurry by mechanical agitation;

b) applying the slurry of a) onto a surface of at least one interdigitated electrode array to form a fine layer of coating;

c) subjecting the applied fine layer of coating of b) to thermal treatment and thereby obtaining a surface coated interdigitated electrode arrays;

d) integrating the surface coated interdigitated electrode arrays of c) with electronic components, and thereby obtaining fully functional sensor with a gas sensing function.

In one embodiment the solvent is a non-polar solvent, selected from the group consisting of toluene, n-hexane, dichloromethane, pyridine, chloroform, and methyl ethyl ketone.

In one embodiment the solvent is a conductive ink, preferably selected from the group consisting of UV curable inks, conductive inks and semi-conducting polymers.

In one embodiment the UV curable inks are dielectric inks.

In one embodiment the conductive inks are selected from the group consisting of silver ink, and carbon ink.

In one embodiment the slurry of step a) comprise sensing material of at least 1 and at most 99%, preferably between 5 to 70%.

In one embodiment the slurry of step 9a) is used to print interdigitated electrode arrays by screen-printing method, wherein the array distance may vary between 100 nm to 1000 µm, preferably between 100 µm to 500 µm.

In one embodiment the coating of step b) is performed by a method selected from the group consisting of dip coating, drop casting, ink jet coating, fluidized bed coating, and spray coating.

In one embodiment the thermal treatment of the surface coated electrodes of step c) is performed at temperatures between room temperature to 120° C., preferably between 40 to 80° C.

The functional devices of the invention are advantageously simple and highly sensitive devices for detecting a range of VOCs in particular to analytes of spoilage food products, indoor and outdoor odors, analytes in clean room conditions, toxic analytes at industrial environments, hydrocarbon gases, and analytes associated with specific disease. Moreover, the present invention relates to a methodology of making robust and highly sensitive sensor printable with existing printing technologies.

The present disclosure relates to a functional device comprising of sensing material and printed electrodes. In addition, the functional devices are easily printable on any substrates with the existing printing technologies. The VOCs may include but not limited to alcohols, aldehydes, ketones, fatty acids, esters and sulphur compounds. The functional device selectively detects the VOCs surrounding the sensing part and quantitatively translates the detected gas concentrations in the form of signal resistance to an electronic component, wherein the electronic components are passive, active or battery-assisted passive. The electronic component wirelessly communicates the signal resistance to portable devices such that the information may be decoded to a text format or an image format.

The invention in one embodiment relates to a sensing part containing a sensing material having a property of sensing volatile organic compounds (VOCs). The sensing material is highly sensitive to many VOCs whose concentrations even below sub-ppm (parts per million). In particular, the sensing material comprises of a composite of mixtures of two or more conductive, non-conductive, semi-conductive and additive materials. The sensitivity of the sensing material varies with the composition of the composite and in particular to the combinations of conductive and semi-conductive material combinations.

The invention also provides a method of making a functional device with a sensing property involving addition of the sensing material to an organic solvent and/or to conductive inks capable of forming slurry; applying the slurry onto the surface of the printed electrodes to form a fine layer of coating, followed by subjecting the applied coating to thermal treatment, to thereby obtaining a surface coated printed electrodes; and finally integrating the functional device with the electronic components, which further enables communication of the sensing property. The method also discloses proper combinations and concentrations for making a slurry; wherein the said combinations may vary subjecting to the sensitivity of the sensor part.

In another embodiment, application of the functional devices in smart packaging is to detect the level of VOCs in a range of sealed food products is also been disclosed. The invention includes a label for application on the outside of the package where one or many tubes punches a hole in the packages exterior which creates access to the atmosphere for the functional device. The tubes may be made of and/or coated with permeable materials to avoid that materials from the sensing unit migrates to the inside of the package. A label for application on the outside, which is placed over a punched hole in the exterior of the package, the label contains a permeable polymer layer to avoid that materials from the sensing unit migrates to the inside of the package. A case, consisting of pillow made of permeable polymer, whereas the sensing unit is placed inside of the pillow. A polymer case where the sensing unit is molded into the case and then coated with a permeable polymer layer.

SHORT DESCRIPTION OF THE DRAWINGS

Figure 1B:
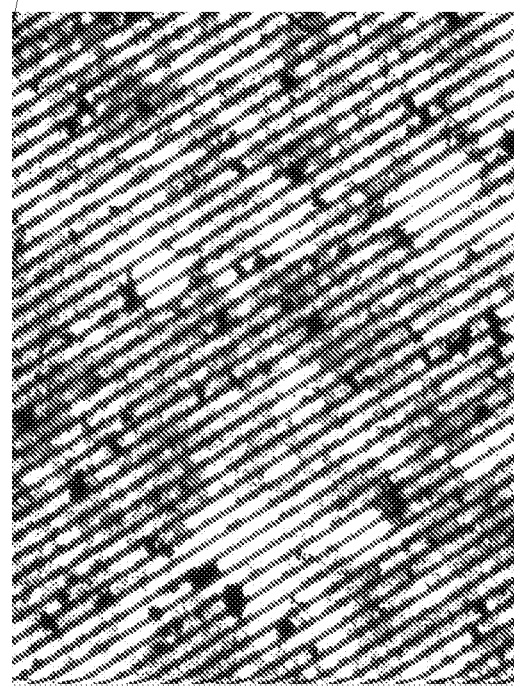

FIG. 1: a) Design of an interdigitated electrode (IDE) which serves as a base for depositing the sensor material, b) Light microscopy image of drop casted sensor material over the electrode arrays.

Figure 2:
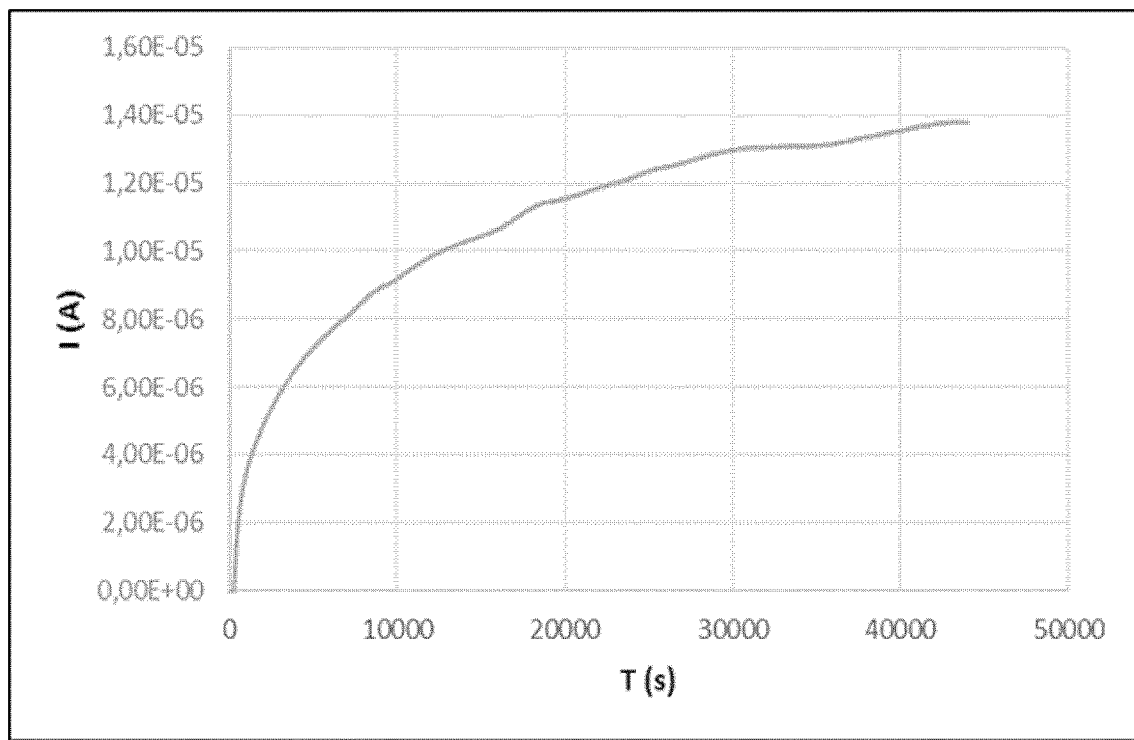

FIG. 2: Amperometric measurements of the IDE sensor, is a plot of current ($\mu A$) as a function of time (Ks) employing one embodiment of the device of the invention in response to Amine gas.

Figure 3:
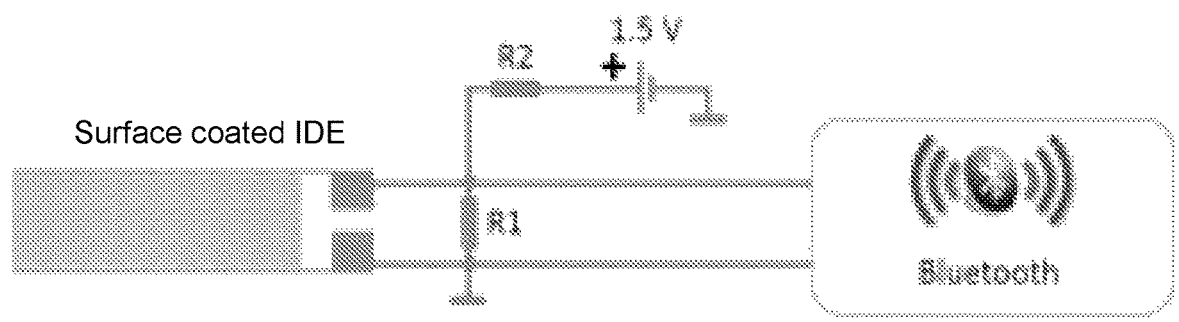

FIG. 3: Circuit design enabling Bluetooth connection of the IDE. The IDE is surface coated. R1, R2 and battery of 1.5 V constitute the divider/transducer and power supplier to IDE sensor. R1=270 k$\Omega$ and R2=4×R1.

DETAILED DESCRIPTION

For convenience and ease of understanding, certain terms used in this invention are defined here.

Functional Device: A device with a sensing function, wherein it contain one or more electrode arrays and a sensing material used to detect and distinguish odors or gases precisely in complex samples or environments and at low-cost.

Functional devices with gas sensing function are of great interest in particular food industry. Because, there are no quantitative means to determine if packaged food is spoiled in the food chain. A common method used for determining the status of meat, on spoilage, is analysis of the counts of total viable bacteria and/or specific spoilage bacteria. However, it is a time consuming and labor intensive process, hence meat producers currently performing the tests on a standard batch and extrapolating the effects to the rest of batches. Functional devices offer most reliable solution to identify the status of the food by detecting volatile organic compounds (VOCs) produced by meat bacteria under storage conditions. They can take measurements in real time, they can be produced cheaply; they can be portable and readily integrated into electronic circuitry without direct visual observation needed to obtain the readout.

The present disclosure envisages a functional device with a gas sensing function and printable process for preparing such device. A combination of sensor material and printed electronic components are previously known and a large variety of combinations have been made targeting gas sensing applications. However, sensitivity and selectivity of the sensor material against targeted gases as well as reproducibility of the sensor function has been a challenge. The present invention solves these issues. The present invention disclose a sensor material comprising a composition that responds to individual VOCs and/or combinations thereof.

The present invention further discloses unique combinations of sensing materials, comprising a composite of a non-conducting material and/or, semiconducting material and/or, conducting material. This allows for a unique feature of the sensor material. These features exclude the invention from the existing sensing materials and their combinations such as crystalline, non-crystalline, organics, inorganics to name a few. In the present invention, a composite of non-conducting material and conducting material comprise a semiconducting feature of the sensor material. Such a composite sensor material shows an increased sensitivity and reproducibility of the functional device.

Other features of the present invention are the selectivity as well as the sensitivity of the sensor material against different VOCs and combinations of VOCs. Sensor materials generally responds to a single VOCs. Targeting multiple VOCs requires combustion of sensor material on the same substrate. However, the present invention disclose a respond to single, multiple as well as complex mixtures of VOCs at extremely low concentration levels. Several examples have been evaluated to prove the function of the present invention, where real time chicken meat samples show a sharp response to the sensor material.

In one aspect of the present disclosure there is provided a functional device comprising of sensing material and interdigitated electrodes. The sensing material is a composite comprising two or more materials wherein one of the materials is optionally an additive, and other materials are selected from the group consisting of non-conducting material, semi-conducting material, and conducting material.

The non-conducting material is synthetic amorphous silica, preferably selected from the group consisting of fumed silica, precipitated porous silica, precipitated non-porous silica and silica aerogel. In addition, non-conducting material is also synthetic titanium dioxide, preferably selected from the group consisting of precipitated porous titanium dioxide, precipitated non-porous titanium dioxide.

The porous properties of the present disclosure are characterized by porosity in the range of 30% to 95%, surface area in the range of 10 m$^2$/g to 900 m$^2$/g, and tapped density in the range of 0.05 g/m$^3$ to 2.0 g/m$^3$. In addition, particle size of the particles may play a crucial role in preparing the sensing material. In the present disclosure, a range of particles of porous and nonporous titanium dioxide, fumed and precipitated porous, -nonporous, and silica aerogels have been used, whose particle size is in the range between 0.3 to 10 microns. All the particles are either spherical, spheroid, amorphous in shape. The non-conducting material may be hydrophobic, which prevents water/humidity from accessing the sensing material but permitting the contaminant to pass through and interact with the sensing material. As result, the hydrophobic nature preserves the function of the sensing material and avoids interference of water with the electrical properties of the sensing material. In various embodiments, hydrophobic-coated non-conducting materials are used, where in the said hydrophobic agent can be selected from the group consisting of organosilicon compounds comprising of alkoxy silanes, silazanes, and silylating agents. In one embodiment the organosilicon compounds are selected from the croup consisting of methyltrimethoxysilane, decyltrimethoxysilane, hexamethyldisilazane, trimethylsilyl chloride, and dimethyloctadecylchlorosilane.

The conducting material is selected from the group consisting of carbon and carbon-based materials, preferably where in the said carbon and carbon-based materials are selected from the group consisting of carbon dots, carbon nanoparticles, carbon sheets, carbon nanotubes and graphenes. The conducting materials improve the conductivity of the sensor material and aid the formulation of the sensing composition. The said carbons have been selected from a range of commercial suppliers, whom properties may vary by their production method. For example, Carbon nanotubes (CNTs) having been used in some of the embodiments belong to single wall CNTs and Multiwall CNTs. In some other embodiments, carbon nanoparticles have been used whose particle size varies between 0.1 to 1 microns. In an embodiment, commercially available graphene is used in the sensor composition, to improve the conductivity of the sensor material.

The semi-conducting material used in the sensor material, wherein the semi-conducting material is a metalloporphyrin dye; preferably the metalloporphyrin dye comprise at least one metal ion selected from the group consisting of $Sc^{3+}$, $Zr^{4+}$, $Lu^{3+}$, $Cr^{3+}$, $Mn^{3+}$, $Fe^{3+}$, $Co^{3+}$, $Mo^{5+}$, $Ru^{2+}$, and $Mg^{2+}$; preferably the metalloporphyrin dye comprise alkyl or aryl groups with R a minimum of 4. The mechanism of porphyrin and other molecules has been extensively discussed in the literature. Due to the metal ion at the centre, porphyrins become more prone to accept electrons from donor molecules such as VOCs (e.g., amines). This gives a charge transfer from the porphyrin to the substrate (conducting/non-conducting material). Therefore, the rate of charge transfer is relying on the metal ion and its electrophilicity. In addition, the sensitivity of the sensor material is also depending on the substrate material such as non-conducting or conducting material. Metalloporphyrins on insulating sensor surface make a semiconducting layer. Upon binding VOCs, the semiconducting porphyrins become more conducting. This results in the current increase (thus lower resistance). On the other hand, Metalloporphyrins on conductive sensor surface make a highly conductive layer. Upon binding VOCs, the porphyrins become less conducting as the total conductivity is less than the initial current. This results in the current decrease (thus higher resistance).

In some of the embodiments, the semiconducting material may be a composite of non-conducting material and conducting material. The non-conducting material may be a synthetic amorphous silica or Silicon (Si) and the conducting material is a Carbon. The molar ratios of non-conducting to conducting material vary between 0.01 to 1, but preferably between 0.2 to 0.6. In the present disclosure, the composite may obtain by synthesizing in-house process. A two-step process may be used to synthesize the composite of synthetic amorphous silica and Carbon, wherein the mixing of two components in toluene and stirring the solution by a mechanical agitation. Finally, filtering the composite using Bucher funnel and drying the composite powder under ambient conditions. In other embodiments, a commercially available Silicon-Carbide was used as it is without any further treatment.

The additive in the sensor material is a binder; preferably one selected from the group consisting of nitrocellulose, polyurethane resins, polyvinylbutyral, PVC-copolymers, ketonic resins, fumaric & maleic resins, polyamides, ethylcellulose (as modifier), and acrylic resins. The concentration of the additive is between 0.1 to 50 weight % of the sensor material, preferably between 0.5 to 10 weight %.

The conductivity of the sensing material varies with the composition of the sensor composite and in particular to the combinations of conductive, non-conductive and semi-conductive material combinations. Preferably, the variations in the concentrations are mainly for conductive and non-conductive materials. In one embodiment the molar concentration is between 0.0005 and 5, preferably between 0.005 and 2, preferably between 0.001 and 1.

In various embodiments, the non-conducting material is used as a substrate for other components of the sensing material composition. Silica coated carbon is one of such material, where the silica coating may change conducting properties of the sensor material. In various embodiments, carbon nanotubes are coated with silica by sol-gel process, where the molar ratios of CNTs to Silica varied between 0.01 to 1. In yet another embodiment of the present disclosure, porous silica containing carbon dots are prepared, where in the carbon particles are embedded in the porous structures of silica by high temperature heat treatment method.

Interdigitated electrode arrays in the present disclosure are printed electrodes, preferably the printed electrode comprise a band/gap between 0.1 to 1000 μm, preferably between 0.1 to 500 μm; preferably between 5 μm to 200 μm. Printed electrodes enable the development of sensors and smart sensing systems with unique characteristics such as flexibility, transparency, and biocompatibility. In addition, environmental friendly materials and process may be employed, thanks to the technology of printed electrodes. Printed electrodes are very attractive for large scale manufacturing at low production cost, which makes them a powerful source for gas sensing applications. Recent technological advantage of printed electrodes is that the array band/gap can be as low as 0.1 μm, which makes them very attractive for extremely high sensitive sensors.

In the present disclosure, the design of interdigitated electrode array consists of a pair of twin electrodes arranged in a comb like structure in which there is a band/gap that is formed between the two electrodes. The output signal strength of Interdigitated electrode arrays is controlled through careful design of the active area, width of each array, and band/gap between electrode arrays. The design contains minimum of 20 electrodes or 10 pairs/bands of comb-like shape with the width of electrodes at a minimum of 100 μm while the length a minimum of 1000 μm. The dimensions for bands/gaps may vary between 0.1 to 1000 μm, preferably between 5 μm to 200 μm. In the present disclosure, there may be geometric differences in the design of the Interdigitated electrode array result in specific electrochemical behavior as well as highly sensitive product.

The printed electrodes may be screen printed or lithographic printed or ink jet printed electrodes. The selection of printing method varies with the electrode array band/gap, ink type and substrate used to print such electrodes. Ink type for printing electrodes is based on carbon, gold, platinum, silver or carbon nanotubes, on substrates such as flexible plastic substrate, ceramic substrate, and glass substrate. In the present disclosure, commercially available Interdigitated electrode arrays may be used, wherein the array distance may vary between 0.1 μm to 1000 μm.

In another aspect of the present disclosure there is provided a process for preparing a functional device, wherein the process comprises of
a) adding the sensing material to a solvent capable of forming slurry by a mechanical agitation;

b) applying the slurry of a) onto a surface of at least one interdigitated electrode array to form a fine layer of coating;

c) subjecting the applied fine layer of coating of b) to thermal treatment and thereby obtaining a surface coated interdigitated electrode arrays;

d) integrating the surface coated interdigitated electrode arrays of c) with electronic components, and thereby obtaining fully functional sensor with a gas sensing function.

In another aspect of the present disclosure there is provided a process for preparing a functional device, wherein the process comprises of e) adding the sensing material to solvents capable of forming slurry by a mechanical agitation;

f) applying the slurry of a) onto a surface of at least one interdigitated electrode array to form a fine layer of coating;

g) subjecting the applied fine layer of coating of b) to thermal treatment and thereby obtaining a surface coated interdigitated electrode arrays;

h) integrating the surface coated interdigitated electrode arrays of c) with electronic components, and thereby obtaining fully functional sensor with a gas sensing function.

Printability of the sensing material is another advantage of the present invention. The sensor material subjected to different combinations of conductive, non-conductive and semi-conductive materials may be printable by addition to solvents and forming a slurry. Further, the sensor material subjected to different combinations of conductive, non-conductive and semi-conductive materials may be printable by addition to solvents and forming a slurry. The present invention discloses making the slurry printable using a mixture of solvents. Innovative step of the present disclosure is also that the solvents are widely used in the current printing industry and allows to adopt the technology without re-establishment of the infrastructure. In one embodiment of the present invention, Screen printed electrodes were made to not only address the issue of cost effectiveness but also satisfy the requirement of portability. Interdigitated electrodes with an array distance between 100 to 1000 μm was prepared and duly tested their compatibility as part of the functional device.

The solvent is selected from the group consisting of, but not limited to, non-polar solvents, said non-polar solvent is selected from the group consisting of toluene, n-hexane, dichloromethane, pyridine, chloroform and methyl ethyl ketone. The solvent may also be solvents. In one embodiment the present invention comprise at least one solvent. In another embodiment the present invention comprise at least two solvents. In yet another embodiment the present invention comprise a mixture of solvents. In addition, the solvent may be a conductive ink, preferably selected from the group consisting of UV curable inks and conductive inks; preferably the UV curable inks are dielectric inks and said conductive inks is selected from the group consisting of silver ink, and carbon ink. Optionally, conductive ink may be selected from semi-conducting polymers. The concentration of the sensor material in the slurry may be at least 1 to 99%, preferably between 5 to 70%. The quantity of sensor material in the slurry may vary depending on the conductive properties of the slurry.

In another embodiment of the invention, the slurry was used as ink for making 100-1000 μm band/gap interdigitated electrodes (IDE) by a screen-printing method. This method facilitates to reduce a process step by a factor and improves the sensitivity by a two-fold factor.

In another embodiment of the invention, the slurry may be used to coat interdigitated electrodes (IDE) of different band/gap. In this case, applying the slurry onto a surface of at least one interdigitated electrode array to form a fine layer of coating. The thickness of the layer may vary on the coating method. In one embodiment of the invention, drop casting was used, where the coating thickness ranges from 50 to 1000 microns, while in another embodiment, dip coating gives a fine layer of sensor material whose coating thickness below 200 microns. Other methods may be used but not limited to such as ink jet coating, fluidized bed coating, and spray coating.

Subjecting the applied coating to a thermal treatment and thereby obtaining a surface coated interdigitated electrode arrays. The thermal treatment is necessary to remove solvents if any in ink after the coating on IDEs. Thermal treatment is conducted in an inert atmosphere or under vacuum at temperatures between room temperature to 120° C., preferably between 40 to 80° C. Thermal treatment is also necessary for the sensor material to adhere on IDE substrates as well as reducing the peeling effect.

Finally, to obtain a fully functional device, the surface coated IDE may be integrated with electronic components, preferably wherein the electronic components are passive, active or battery-assisted passive tags, preferably wherein the said components frequency range between 9 KHz to 3000 GHz, preferably between 13.56 MHz to 960 MHz. The electronic component wirelessly communicates the signal resistance to portable devices such that the information may be decoded to a text format or an image format. The electronic components may include electronic transducers for converting electrical resistance in the IDE circuit to a frequency of the tags.

A variety of electronic transducers may be applied in the present disclosure. Resonant LCR (inductor-capacitor-resistor) transducer is one of such component. LCR transducers are highly conducting circuits in contact with an IDE. The mechanism of operation of these sensors involves the analyte-induced changes to the dielectric constant of the sensing material and correlation of these changes with changes in the frequency and attenuation response of the sensor.

Other electronic components such as Radio frequency identification (RFID) tags may be used, due to its advantages of simultaneous tag reading, wider reading range and faster data transfer. A combination of tags with a specific function has already been developed including temperature sensor, moisture sensors, gas sensors, and Bio-sensors, to name a few.

The selection of tag type broadly depends on the frequency range and manufacturing cost of the tag including power source, transmitter, and reader antennas. Active tags have their own transmitter and power source. Usually, the power source is a battery, and it can also be solar. Active tags broadcast their own signal to transmit the information stored on their microchips. An active RFID system typically operates in the ultra-high frequency (UHF) band, covers a frequency range from 300 MHz to 3 GHz and read from distances of 100 feet or more.

In another implementation, passive tags may be used for making a functional device of the invention. Passive tags with no internal power source and instead are powered by the electromagnetic energy transmitted from a reader. Passive tags can operate in the low frequency (LF), high frequency (HF) or ultra-high frequency (UHF) radio bands, typically between 125 kHz to 960 MHz.

In yet another implementation, battery assisted passive tags may be used for making a functional device of the invention. As the name says, Battery Assisted Passive tag is a type of passive tag, which incorporates an active tag feature.

In some case, amplifying the output current signal may be necessary to reach the resistance detectable for tags. Two or more transistors include an impedance transistor and a buffer transistor used to amplify the output signal and may be integrated into a sensor circuit. A range of transistors may be used including most advanced transistor such as organic electrochemical transistor as well as classical transistor such as a metal-oxide-semiconductor transistor.

The functional device disclosed in the present invention can reach out to different applications and product categories such as process monitoring, shelf-life investigation, freshness evaluation, and other quality control studies. One embodiment of invention is to use the functional device to monitor freshness or spoilage of different food raw material and products. In particular, fresh foods where significant release of volatiles occur during handling and storage due to rapid degradation by bacterial processes, such as meats, oysters, eggs, shrimps, and fish. In a more robust use of the functional device is to monitor the status of freshness or spoilage along the whole value chain including from slaughtering stage to packaging and finally to consuming stage.

In a preferred embodiment of the invention, process monitoring includes but not limited to alcohol (including wine, beer, whiskey, vodka) fermentation process, microbiological processes involved in food production, i.e. to screen the aroma generation of lactic acid bacteria strains in the production of cheese and other fermented dairy products. The functional device may also be used to monitor the ripening process of fruits and other vegetables during their shelf-life period (from harvest until consumption).

In another preferred embodiment of the invention to use for identification purposes, include olive oil, cheese, honey, vegetable oil, fruit juices and vinegars. The identification and determination of geographical origins, among them, wines from Spanish, Italian, and French are of interest.

In another preferred embodiment of the invention, the functional device may be used for monitoring clean room environment.

In another preferred embodiment of the invention, the functional device may be used to detect a gas leak, particularly highly flammable gases and low boiling point gases such as, but not limited to (toxic-) industrial gases and hydrocarbon gases. Examples of (toxic-) industrial gases include but not limited to ammonia, carbon dioxide, hydrogen chloride, and sulphur dioxide; examples of hydrocarbon gases include but not limited to Methane, Butane, Propane, or mixture of them. In this aspect, the functional device may be attached to the cylinders that carries the gases. In particular, LPG cylinders supplied for household have high rate of leak at the regulator and other possible leaks from the flow carriers. The functional device detects the gas leak and alerts the user through an audio signal.

In a preferred embodiment of the invention, application of the functional devices in smart packaging products is been disclosed. Smart packaging allows monitoring of the properties of packaged foods and their environment, and communicating their state throughout the value chain and inform to the manufacturer, retailer, and consumer. In this regard, the functional device has to access the headspace of the package, where the functional device may monitor certain type and certain amount of gases releases during spoilage. The gases most commonly identified in packaged meat during handling and storage include alcohols, aldehydes, ketones, fatty acids, esters and sulphur compounds. Introducing sensor materials and electronic components to the packaged meat products, particularly fresh meat products may need to compromise the food safety issues and regulations associated with the registration. A smart packaging method may require allowing the functional device in contact with the food products. In this regard, a smart label is being proposed in the invention.

In one preferred embodiment of the invention, the smart label comprises a semi-permeable membrane where an adhesive material one side of the membrane enables to adhere to a lidding film or sealing film and sensor material on the other side of the label enables to access the gasses that diffuse out from the packaged food. The semipermeable membrane is permeable to analyte gasses, as well as water vapour, but do not allow bacteria and water to pass through. The label enables to reach headspace in the packages while keeping the functional device components on the outside of the package. Over the sensor material, an interdigitated electrode (IDE) to track any conductivity changes of the sensor material due to analyte gases. The IDE may further be connected to electronic components for transmitting the information of the status of the food in the packaged product to a wireless reader. The label may be printed in combination with the lidding films/sealing films and can be used to seal a range of the packaged food containers. The label may also be integrated with other packaging solutions such as shrink barrier bags, shrink barrier films, vacuum packaging films, and thermoforming films.

In a preferred embodiment of the invention includes a label for application on the outside of the package, where on one side of the label one or many tubes/needles creating permeability with an adhesive material to adhere to a packaging film. On the other side of the label, there is a sensing material continually accessing the headspace gasses via the permeable space. The label may create one or many holes in the packaging film thereby access the headspace of the sealed food package. The invention leads to a simple label placed on a package, and information of the status of the food can still be accessible by a wireless reader. The label includes a packaging film and a functional device, wherein packaging film may be selected from different plastics, polymers and metals such as but not limited to polypropylene (PP) and derivatives, polyester (PET) and derivatives, polyethylene (PE) and derivatives, and aluminium. The functional device further comprises of sensing material, interdigitated electrodes and electronic components.

EXAMPLES

1. Preparation of Sensor Material

The sensor material is a composite of mixture of materials, wherein one of the materials is optionally an additive, and other materials are selected from the group consisting of non-conducting material, semi-conducting material, conducting material. All metalloporphyrin dyes used in the process were purchased from Sigma-Aldrich and used as it is.

A typical sensor material may be prepared as follows.

(1a). In a 50 ml round bottom flask, 0.1 g of 5,10,15,20-Tetrakis (pentafluorophenyl)-21H,23H-porphyrin iron(III) chloride was dissolved in 10 ml of toluene, under stirring, at room temperature to obtain a reaction mixture. After 1 hour of stirring, 1 g of porous silica particles were added to the mixture and continue to stir for another 1 hr. The porous silica particles were made in-house with characteristics such as pore size of 70 Å, the surface area of 650 m2/g and particle size of below 1 microns. To the mixture, 0.01 g of chemically inert polyvinylidene fluoride (PVDF) was added to improve the adhesion properties of the sensor material. Finally, the solvent was evaporated by a rotary evaporator, and stored in a sealed container for further use.

(1b). In another embodiment of the present invention, the sensor material may also be prepared with the following combinations.

In a 50 ml round bottom flask, 0.15 g of the silica-carbon composite was dissolved in 10 ml of pyridine under stirring, at room temperature to obtain a reaction mixture. Preparation of silica-carbon composite involves the addition of porous silica particles to carbon nanoparticles at a molar ratio of 0.45 in a polar solvent such as 2-propoanol and stirring the mixture for 6-8 hours at 60° C. The porous silica particles were made in-house with characteristics such as pore size of 30 Å, the surface area of 420 $m^2/g$ and particle size of below 300 nanometers. Finally, evaporation of the solvent by rotary evaporator to obtain a composite of silica-carbon with semiconducting properties.

After 1 hour of stirring the silica-carbon composite solution, 0.5 g of ethyl cellulose (viscosity 10 cP, 5% in toluene/ethanol 80:20 (lit.), extent of labelling: 48% ethoxyl) was added to improve the adhesion properties of the sensor material. Finally, the solvent was evaporated by a rotary evaporator, and stored in a sealed container for further use.

(1c). In another embodiment of the present invention, the sensor material may also be prepared with the following combinations.

In a 50 ml round-bottom flask, 0.09 g of Zinc 5,10,15,20-tetra(4-pyridyl)-21H,23H-porphine was dissolved in 8 ml of dichloromethane (DCM), under stirring, at room temperature to obtain a reaction mixture. After 1 hour of stirring, 0.15 g of porous titanium dioxide were added to the mixture and continue to stir for another 1 hr. The porous silica particles were made in-house with characteristics such as pore size of 45 Å, the surface area of 210 $m^2/g$ and particle size of below 800-1000 nanometers. To the mixture, 0.01 g of chemically inert polyvinylidene fluoride (PVDF) was added to improve the adhesion properties of the sensor material. Finally, the solvent was evaporated by rotary evaporator, and stored in a sealed container for further use.

(1d). In another embodiment of the present invention, the sensor material may also be prepared with the following combinations.

In a 50 ml round-bottom flask, 0.12 g of Iron (III) phthalocyanine chloride was dissolved in 12 ml of dichloromethane (DCM), under stirring, at room temperature to obtain a reaction mixture. After 1 hour of stirring, 0.56 g of carbon nanotubes (MWCNTs) were added to the mixture and continue to stir for another 1 hr. The CNTs were purchased from commercial suppliers with a characteristic such as tube length of 5 to 20 microns and tube diameters between 0.1 to 0.5 microns, surface area of 135 $m^2/g$. To the mixture, 0.01 g of chemically inert polyvinylidene fluoride (PVDF) was added to improve the adhesion properties of the sensor material. Finally, the solvent was evaporated by rotary evaporator, and stored in a sealed container for further use.

2. Method of Making a Functional Device

Method of making a functional device according to current disclosure involves forming slurry of a sensor material; forming a layer of coating on the interdigitated electrode (IDE) array and integrating the surface coated IDE arrays with electronic components to obtain a fully functional device.

For exemplification of the functional device, the sensor materials described in the example 1 were used. The electronic components may be a Bluetooth device or an NFC tag.

(2a). For making a functional device, first the sensor material (any of the example 1a, 1b, and 1c) is mixed with non-polar solvents such as methyl ethyl ketone and hexane. In a preferred embodiment, the slurry consists of at-least 50% of the sensor material. The slurry was then coated on an IDE array by a drop casting method; where in 15 μl of slurry was used to coat the electrode surface. The Interdigitated electrodes are gold plated electrodes with an array gap of 10 μm, and the electrodes are commercially available (supplied by DropSens). Prior using the electrode, the surface was cleaned with ethanol and dried at 40° C. oven. After drop casting the slurry on the electrode, subjecting the electrode to thermal treatment at 80° C. oven and thereby obtaining a surface coated interdigitated electrode. FIG. 1 shows Light Microscopy image of the interdigitated electrode with a distribution of the slurry over electrode arrays.

(2b). In another embodiment of the invention, slurry was used as ink for making 100-1000 μm band/gap interdigitated electrodes (IDE) by screen-printing method. The quality of the screen-printed IDEs has been assessed by measuring their resistance. The slurry thus prepared is a combination of a silver ink, and sensor material (as exemplified above 1a) by mechanical agitation for 2 hours at room temperature. The slurry consists of at-least 70% of the sensor material. By screen-printing method, interdigitated electrode with a band/gap of 200 μm was prepared, where the size of the electrode is 7.4×30.2 mm, other sizes may be screen-printed and used for improved signal strength. In another embodiment of the invention, the slurry may be coated directly on an interdigitated electrode, where the electrode surface is fully coated with the slurry.

(2c) Detection sensitivities were initially screened by connecting the surface-coated IDE to a IVIUM potentiostat in a two-electrode configuration and amperometric measurements at 10 mV applied voltage were performed. The measurements were performed in a closed chamber, where the IDE was exposed to different concentrations of analyte gas such as ammonia (one of the VOCs), with maximum range 500,000 ppm, lowest being 1 ppm. Upon exposure, the conductive properties of the sensor material lead to a change in the current over a period of time, which can range as small as about 1 nA to about 100 mA. Even small changes can be detected and therefore these changes in the conductivity of the sensor material can be easily correlated to the presence of the targeted VOCs. FIG. 2 shows a response curve obtained by exposing to ammonia gas, in particular the current response is based on diffusion, wherein the conductivity of the sensor material varies with the longer exposure to VOCs. The recorded current can be used to calculate the resistance of the electrode exposed to air in the absence and the presence of VOCs. The setup is perfect for measuring the kinetics of the sensor response, stability of the response, estimation of noise level, etc. In another implementation, an analysis chamber can be used, where continue doses of VOCs may be exposed to the IDE, in particular to estimate the threshold resistance of the sensor material.

(2d). To obtain a fully functional device with a gas sensing function, integration of the surface coated interdigitated electrode arrays with electronic components such as passive, active or battery-assisted passive tags, preferably wherein the said components frequency range between 9 KHz to 3000 GHz, preferably between 13.56 MHz to 960 MHz.

In a preferred embodiment of the invention, the surface coated interdigitated electrode (IDE) was connected to Bluetooth device comprising voltmeter. Circuit design enabling Bluetooth connection of the IDE is shown FIG. 3. The IDE sensor and the Bluetooth unit is interfaced by simple servitor divider, which converts charged IDE sensor resistance into changes of voltage which is measured by Bluetooth voltmeter. The components of the device can be connected by a mechanical soldering or by electric paint. This design allows working with any of the sensor material. Specifically, it can handle broad range of sensor materials disclosed in the invention. The voltage that drops on IDE-R1 parallel coupling depends on the amount of VOCs sensed by the sensor material. By tuning the sensor material resistivity and the sensitivity of the IDE sensor to VOCs, the R1 can be excluded, which makes the device even simpler.

The response of IDE connected to the Bluetooth device is monitored by exposing surface coated IDE to chicken samples. The chicken samples were freshly purchased from a store; whose size was 1 kg and 350 grams. The date of expiry (DOE) was noted prior the experiments and the measurements were performed before and after the DOE. These experiments were performed to determine the reliability of DOE mentioned on the meat package. The IDE may be incorporated inside the meat package, where the electrodes access overhead space on the package and further sealed to avoid any leak from the package. The electronic Bluetooth may be set outside the package for monitoring the device response. The presence of the VOCs in ambient air surrounding the sensor IDE will cause a change in conductivity in the device of the invention.

As may be seen from the above, the present invention may comprise various design and forms and also various standard circuit components and is not to be seen as limited by a specific embodiment, but rather to be seen as embodying different forms of the functional device.

The invention claimed is:

1. A functional device, comprising:
    a functional sensor, comprising a sensor part and interdigitated electrode arrays,
    wherein the sensor part comprises a sensing material and the interdigitated electrode arrays are printed electrodes,
    wherein the sensing material is a composite comprising an additive and at least one second material, and
    wherein the at least one second material satisfies (i) and/or (ii):
    (i) the at least one second material comprises at least one non-conducting material selected from the group consisting of fumed silica, precipitated porous silica, precipitated non-porous silica, silica aerogel, precipitated porous titanium dioxide, and precipitated non-porous titanium dioxide;
    and/or
    (ii) the at least one second material comprises at least one semi-conducting material selected from the group consisting of a metalloporphyrin dye, a composite of silica and carbon, and a composite of silicon and carbon,
        wherein the composite of silica and carbon and the composite of silicon and carbon have a molar ratio between Si to C that varies between 0.2 to 0.6, and
        wherein the metalloporphyrin dye comprises alkyl or aryl groups as R groups and a minimum of 4 R groups are present, and/or wherein the metalloporphyrin dye comprises at least one metal ion selected from the group consisting of $Sc^{3+}$, $Zr^{4+}$, $Lu^+$, $Cr^{3+}$, $Mn^{3+}$, $Fe^{3+}$, $Co^{3+}$, $Mo^{5+}$, $Ru^{2+}$, and $Mg^{2+}$.

2. The functional device of claim 1, comprising the additive, wherein said additive is a binder.

3. The functional device of claim 2, wherein the binder is at least one selected from the group consisting of nitrocellulose, polyurethane resins, polyvinylbutyral, PVC-copolymers, ketonic resins, fumaric resins, maleic resins, polyamides, ethylcellulose, and acrylic resins.

4. The functional device of claim 1, wherein the printed electrodes are arranged at a distance, wherein the distance may vary between 100 nm to 1000 µm.

5. The functional device of claim 4, wherein at least one of the printed electrodes is selected from the group consisting of screen printed electrodes, lithographic printed electrodes, and ink jet printed electrodes.

6. The functional device of claim 1, wherein the functional device is integrated with one or more electronic components.

7. The functional device of claim 6, wherein at least one of the electronic components is selected from the group consisting of passive tags, active tags, battery-assisted passive tags, and a circuit comprising two or more transistors.

8. A method of making the functional device according to claim 1, wherein the method comprises:
    a) adding a sensing material to a solvent capable of forming a slurry by mechanical agitation;
    b) applying the slurry of a) onto a surface of at least one interdigitated electrode array to form a fine layer of coating;
    c) subjecting the applied fine layer of coating of b) to thermal treatment and thereby obtaining at least one surface coated interdigitated electrode array; and
    d) integrating the at least one surface coated interdigitated electrode array of c) with an electronic component, thereby obtaining a fully functional sensor with a gas sensing function.

9. The method according to claim 8, wherein the solvent is a non-polar solvent, selected from the group consisting of toluene, n-hexane, dichloromethane, pyridine, chloroform, and methyl ethyl ketone, and/or
    wherein the solvent is a conductive ink.

10. The method according to claim 8, wherein the slurry of a) comprises the sensing material of at least 1% and at most 99%.

11. The method according to claim 8, wherein the interdigitated electrode arrays are formed by a screen-printing method, wherein the array distance may vary between 100 nm to 1000 µm.

12. A method of making a functional device, the method comprising:
    a) adding a sensing material to a solvent capable of forming a slurry by mechanical agitation;
    b) applying the slurry of a) onto a surface of at least one interdigitated electrode array to form a fine layer of coating;
    c) subjecting the applied fine layer of coating of b) to thermal treatment, thereby obtaining at least one surface coated interdigitated electrode array; and
    d) integrating the at least one surface coated interdigitated electrode array of c) with an electronic component, thereby obtaining a functional device with a fully functional sensor with a gas sensing function,
    wherein the functional sensor comprises a sensor part and the at least one surface coated interdigitated electrode array, wherein the sensor part comprises the sensing material,
wherein the at least one surface coated interdigitated electrode array is a printed electrode,
wherein the sensing material is a composite comprising two or more materials, wherein one of the materials is an additive and the other materials are selected from the group consisting of a non-conducting material, a semi-conducting material, and a conducting material, and
wherein the composite comprises the non-conducting material, and wherein the non-conducting material is at least one selected from the group consisting of a synthetic amorphous silica and synthetic titanium dioxide, and/or
wherein the composite comprises the conducting material, and wherein the conducting material is at least one selected from the group consisting of carbon and carbon based materials, and/or
wherein the composite comprises the semi-conducting material, and wherein the semi-conducting material is a metalloporphyrin dye and/or wherein the semi-conducting material is a composite of silica, or silicon, and carbon wherein the molar ratio of composite between Si to C varies between 0.01 to 1.

* * * * *